(12) United States Patent
Ju et al.

(10) Patent No.: US 7,022,509 B2
(45) Date of Patent: *Apr. 4, 2006

(54) GAS VESICLES OF CELLS AND METHODS OF HARVESTING, ISOLATING AND MODIFYING SAME

(75) Inventors: Lu-Kwang Ju, Akron, OH (US); Anand Sundararajan, Lexington, KY (US); Sunil Kashyap, Salinas, CA (US)

(73) Assignee: The University of Akron, Akron, OH (US)

( * ) Notice: Subject to any disclaimer, the term of this patent is extended or adjusted under 35 U.S.C. 154(b) by 423 days.

This patent is subject to a terminal disclaimer.

(21) Appl. No.: 10/143,079

(22) Filed: May 10, 2002

(65) Prior Publication Data

US 2002/0132312 A1 Sep. 19, 2002

Related U.S. Application Data

(60) Division of application No. 09/489,386, filed on Jan. 21, 2000, now Pat. No. 6,413,763, which is a continuation-in-part of application No. 08/968,283, filed on Nov. 12, 1997, now Pat. No. 6,036,940.

(60) Provisional application No. 60/029,432, filed on Nov. 12, 1996.

(51) Int. Cl.
*A61B 8/00* (2006.01)
*C12N 1/00* (2006.01)
*C12N 1/20* (2006.01)
*C12N 5/00* (2006.01)
*C12N 5/02* (2006.01)

(52) U.S. Cl. ............ 435/243; 424/9.52; 424/450; 424/451; 424/455; 435/41; 435/252.1; 435/253.6; 435/317.1; 435/325; 435/822; 435/832; 435/946; 210/600

(58) Field of Classification Search ............... 424/1.21; 435/243, 822
See application file for complete search history.

(56) References Cited

U.S. PATENT DOCUMENTS

| 5,487,390 A | 1/1996 | Cohen |
| 5,498,421 A | 3/1996 | Grinstaff |
| 6,036,940 A | 3/2000 | Ju et al. |

OTHER PUBLICATIONS

Walsby, *Nature*, p. 224, 716, (1969).
Walsby, *Microbiol. Rev.*, p. 94, (1994).
Tseng, et al., *J. Chin. Inst. Environ. Egn.*, vol. 6, (No. 71), (1996).
Konopka, et al., "Isolation and Characterization of Gas Vesicles from *Microcyclus aquaticus,*" *Archives of Microbiology*, vol. 112, p. 133-140, (1977).
Zevenboom, et al., "Growth and Photosynthetic Response of the Cyanobacterium *Microcystis aeruginosa* in Relation to Photoperiodicity and Irradiance," *Archives of Microbiology*, vol. 139, p. 232-239, (1984).
Oliver, et al., "The Sedimentation of Buoyant Microcystis Colonies Casued by Precipitation with an Iron-Containing Colloid," *Proc. R. Soc. Land B.*, vol. 223, p. 511-528, (1985).
Kromkamp, et al., "Buoyancy Regulation in a Strain of *Aphanizomenon flos-aquae* (Cyanophyceae): The Importance of a Carbohydrate Accumulation and Gas Vesicle Collapse," *Journal of General Microbiology*, vol. 132, p. 2113-2121, (1986).
Gerloff, et al., "The Isolation, Purification, and Culture of Blue-Green Algae," *American Journal of Botany*, vol. 37, p. 216-218, (1950).
Kratz, et al., "Nutrition and Growth of Several Blue-Green Algae," *American Journal of Botany*, vol. 42, p. 282-287, (1955).
Smith, et al., "Growth and Gas-Vacuole Development in Vegetative Cells of *Anabaena flos-aquae,*" *Archiv. fur Mikrobiologie*, vol. 58, p. 117-126, (1967).

(Continued)

*Primary Examiner*—David M. Naff
*Assistant Examiner*—Deborah K. Ware
(74) *Attorney, Agent, or Firm*—Roetzel & Andress,LPA; George W. Moxon, II (57) ABSTRACT

A method for removing a gas from a site comprising placing cells having gas vesicles under conditions that induce the cells to float to a surface of an aqueous medium, harvesting the cells from the surface of the medium, lysing the cells, separating the gas vesicles from the lysed cells, crosslinking the gas vesicles with a crosslinking agent, loading a gas with a lowered partial pressure for the compound to be removed into the gas vesicles, and placing the gas vesicles such that the gas compound is removed from the site. Harvesting gas-vesicle-containing cells is achieved by placing the cells under conditions that induce the cells to rise to the surface of an aqueous medium—such as darkness, exponential growth stage, flocculation, or dissolved gas flotation—then collecting the cells from the surface of the medium. Gas vesicles are isolated by lysing the cells and separating the gas vesicles from the lysate. Once the gas vesicles are isolated, they can be modified, such as by crosslinking with glutaraldehyde.

10 Claims, 9 Drawing Sheets

OTHER PUBLICATIONS

Walsby, et al., "Changes in Buoyancy of a Planktonic Blue-Green Algae in Response to Light Intensity," *British Phycological Society*, vol. 15, p. 311-319, (1980).

Booker, et al., "Bloom Formation and Stratification by a Planktonic Blue-Green Algae in an Experimental Water Column," *British Phycological Society*, vol. 16, p. 411-421, (1981).

Sebba, et al., "Separations Using Colloidal Gas Aphrons," *2nd International Congress of Chemical Engineering*, p. 27-31, (1981).

Michelsen, et al., "In-Situ Biological Oxidation of Hazardous Organics," *Environmental Progress*, vol. 3 (No. 2), p. 103-107, (1984).

Michelsen, et al., "In-Situ Biodegradation of Dispensed Organics Using a Microdispersion of Air in Water," *Site Remediation*, p. 291-298, (1985).

Kromkamp, et al., "Buoyancy Regulation in Light-Limited Continuous Cultures of *Microcystis aeruginosa*," *Journal Plankton Research*, vol. 10 (No. 2), p. 171-183, (1988).

Bar-Or, et al., "Cyanobacterial Flocculants," *Methods in Enzymology*, vol. 167, p. 616-672, (1988).

Wheatley, et al., "Contrast Agents for Diagnostic Ultrasound: Development and Evaluation of Polymer-Coated Microbubbles," *Biomaterials*, vol. 11, p. 713-717, (1990).

Hayes, et al., "Gas Vesicles are Strengthened by the Outer-Surface Protein, GvpC," *Archives of Microbiology*, p. 229-234, (1991).

Bender, et al., "Characterization of Metal-Binding Bioflocculants Produced by the Cyanobacterial Component of Mixed Microbial Mats," *Applied and Environmental Microbiology*, vol. 60 (No. 7), p. 2311-2315, (1994).

Joseph S. D'Arrigo, "Glycoprotein Surfactants Stabilize Long-Lived Gas Microbubbles in the Environment," *Microbial Enhanced Oil Recovery*, vol. 18, p. 124-140.

Kashyap, Sunil, Sundararajan, Anand, and Ju, Lu-Kwang. "Flotation Characteristics of Cyanobacterium *Anabaena flos-aquae* for Gas Vesicle Production." *Biotechnology and Bioengineering*, vol. 60, No. 5, pp. 636-641 (Dec. 5, 1998).

GAS VESICLES OF CELLS AND METHODS OF HARVESTING, ISOLATING AND MODIFYING SAME

This application is a divisional application of U.S. Ser. No. 09/489,386, filed Jan. 21, 2000, which is a continuation-in-part of U.S. Ser. No. 08/968,283, filed Nov. 12, 1997, now U.S. Pat. No. 6,036,940, which claims the benefit of the filing date under 35 U.S.C. §119(e) of United States Provisional Application for Patent Ser. No. 60/029,432, filed Nov. 12, 1996.

TECHNICAL FIELD

This present invention relates generally to microbubbles and, more particularly, to naturally occurring gas vesicles. Specifically, the present invention relates to methods for delivering or removing a gas to or from a site using these naturally occurring gas vesicles as well as methods for harvesting, modifying, and exploiting the same for various applications. Because the methods of the present invention also entail modifying the naturally occurring gas vesicles, the present invention further relates to semi-synthetic gas vesicles. Compositions of matter comprising these gas vesicles are also disclosed.

BACKGROUND OF THE INVENTION

Microbubbles, encompassing both natural and synthetic gas-filled microcavities, are well known in the art. For example, gas-filled microcavities have been employed for enhanced oil recovery, as contrast agents in diagnostic ultrasound, as reagents in in situ bioremediation of contaminated ground water, and as flotation devices for the separation of minerals.

Microbubbles used heretofore in the art have been synthetic in nature. That is, microbubbles have been produced by methods such as passing air through a surfactant solution. One known technique provides a rapid flow of a dilute surfactant solution through a venturi throat through which gas is emitted to generate the surfactant-stabilized microbubbles. Another example includes employing a triple-barreled jet head that allows for the simultaneous development of an alginate drop and injection of an air bubble inside the drop. Depending on the production type, these microbubbles have been referred to as microballoons, colloidal gas aphrons, micro gas dispersions, and microfoams.

Although synthetically produced microbubbles are well known in the art, they have several shortcomings. Namely, synthetically produced microbubbles lack consistency of size, have poor stability and mechanical strength, and are often biologically incompatible.

Naturally occurring microbubbles, such as gas vesicles, are also known. Many organisms produce and/or employ microbubbles for various biological functions. Specifically, ecological studies show that many microorganisms living in aquatic systems utilize microbubbles as buoyancy devices. Their importance in providing buoyancy for planktonic cyanobacteria and helping them perform vertical migration in lakes and other aquatic systems has been widely recognized. Additionally, they are postulated to play a role in light shielding, as well as providing the cell with the ability to alter its configuration to increase cell surface area as a function of volume.

Among the difficulties in utilizing naturally occurring microbubbles for commercial purposes is the fact that it is difficult to harvest them. For example, in typical industrial microbial fermentations, cells are collected by either filtration or centrifugation. Filtration involves large pressure gradients or mechanical forces that tend to collapse the gas vesicles, and centrifugation is inefficient because the vesicle-bearing cells often have densities very close to that of water. Further, where centrifugal force is strong enough to achieve efficient cell collection, such forces often destroy the gas vesicles. It is also difficult to sterilize them so that they can be kept stable against microbial and enzymatic attack.

Biological systems often produce gaseous compounds as by-products of their metabolism. When these compounds accumulate, they can inhibit the growth, product synthesis and even survival of the biological system. A common example of such a gaseous compound is carbon dioxide. If it is not removed effectively, carbon dioxide accumulation can negatively affect plant cell cultures, insect cell cultures, animal cell cultures, and microbial fermentations. Furthermore, the low shear requirements of many types of cell culture lead to poor gas-liquid interfacial transfer and, consequently, potential accumulation of inhibitory or toxic gaseous metabolic by-products.

Thus, there is a need in the art to overcome the shortcomings of synthetically produced microbubbles. Further, there is a need in the art to overcome the difficulties in harvesting naturally occurring microbubbles and utilizing such microbubbles for commercial purposes in lieu of synthetic microbubbles. Still further, there is a need in the art to overcome the difficulties associated with the removal of gaseous metabolic by-products from biological systems.

SUMMARY OF INVENTION

It is therefore an object of the present invention to provide purified gas vesicles for use in delivery or removal of a gas to or from a site.

It is another object of the present invention to provide semi-synthetic microbubbles with improved strength or improved stability.

It is yet another object of the present invention to provide crosslinked gas vesicles in a sterile suspension.

It is a further object of the present invention to provide a method for harvesting naturally occurring microbubbles.

It is another object of the present invention to provide a method for modifying naturally occurring microbubbles to produce semi-synthetic microbubbles.

It is still another object to provide a method for delivering or removing a gas using semi-synthetic microbubbles.

It is yet another object to provide a method for delivering oxygen or other desirable gaseous compounds or for removing undesirable gaseous compounds from a cell or tissue culture via semi-synthetic microbubbles.

At least one or more of the foregoing objects, together with the advantages thereof over the known art relating to microbubbles, which shall become apparent from the specification which follows, are accomplished by the invention as hereinafter described.

In general, the present invention provides a method for delivering a gas to a site, or alternatively, for removing a gas from a site, comprising placing cells having gas vesicles under conditions that induce the cells to float to a surface of an aqueous medium, harvesting the cells from the surface of the medium, lysing the cells, separating the gas vesicles from the lysed cells, and crosslinking the gas vesicles with a crosslinking agent. In removing a gas, the method requires the additional step of loading the gas vesicles with a gas that has a higher partial pressure for the gas to be delivered and/or that has a lower partial pressure of the compound or compounds to be removed from the site, and placing the gas vesicles such that the gas to be delivered partitions from the vesicles and the gas to be removed partitions into the vesicles.

The present invention also provides a method of harvesting gas-vesicle-containing cells comprising placing cells having gas vesicles under conditions that induce the cells to float to a surface of an aqueous medium, and harvesting the cells from the surface of the medium.

The present invention further provides isolated gas vesicles comprising a medium having extracellular gas vesicles, preferably crosslinked, and having improved strength or improved stability.

PREFERRED EMBODIMENT FOR CARRYING OUT THE INVENTION

The present invention involves the production, modification and application of naturally occurring gas-filled microcavities. For purposes of this disclosure, these gas-filled microcavities will be referred to as gas vesicles, or in the case where they have been modified, semi-synthetic gas vesicles. Naturally occurring gas vesicles are those preferably found within living organisms. Most preferably, these gas vesicles are located within the cell or cells of living organisms and are often found as a group of vesicles or a vacuole. Gas vesicles can occupy up to about 10% of the cell volume. The best known examples of gas-vesicle-containing cells are those of cyanobacteria, halobacteria, and phototrophic bacteria.

Figure 1A:
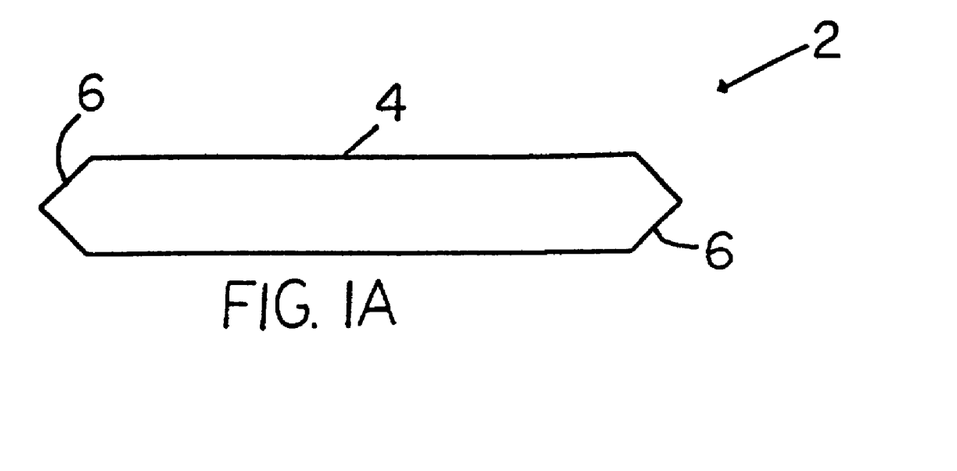
FIGS. 1A and 1B are a schematic side view and end view, respectively, of a cyanobacterium gas vesicle.
Figure 1B:
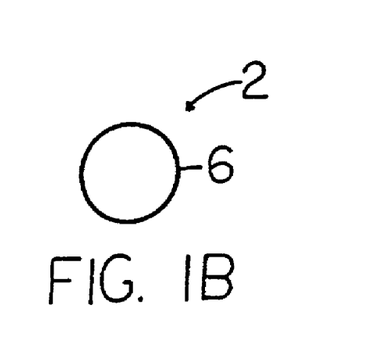

As depicted in FIGS. 1A and 1B, gas vesicles 2 are proteinaceous structures that are usually shaped as hollow cylindrical tubes 4 closed at each end by a hollow conical cap 6. These structures are typically hydrophobic, thereby preventing the penetration of water and other polar liquids by surface tension, but are permeable to gas molecules. Due to their permeability, the interior of the vesicles become filled with the gas or gases contained in the surrounding environment; typically, the gases are dissolved in a surrounding aqueous environment. Further, it is believed that these structures gain their dispersability in aqueous media from hydrophilic proteins attached to the outer surfaces of the gas vesicles.

Typically, the walls of naturally occurring gas vesicle structures are quite rigid and withstand considerable hydrostatic pressure with little change in overall volume. The various sizes of the reported gas vesicles range from about 340 to about 750 nm in length and from about 60 to about 110 nm in width, depending on their biological sources. The wall thickness of such gas vesicles is typically about 2 nm. The submicron size of gas vesicles and their inherent strength and stability give them a substantial advantage over synthetically produced microbubbles.

It should be understood that a variety of naturally occurring gas vesicles can be employed in the present invention. For example, they can be obtained from various procaryotes, including cyanobacteria such as *Microcystis aeruginosa, Aphanizomenon flos aquae* and *Oscillatoria agardhii*; phototropic bacteria such as *Amoebobacter, Thiodictyon, Pelodictyon,* and *Ancalochloris*; nonphototropic bacteria, such as *Microcyclus aquaticus*; and archaea, such as *Haloferax mediterranei, Methanosarcina barkeri, Halobacteria salinarium*. Preferred procaryotes are filamentous, for ease of separation, and have high vesicle content, by volume, for greater gas delivery or removal capability. Therefore, *Anabaena flos aquae*, where the vesicles comprise about 10% of the volume of the cell, is a preferred source of naturally occurring gas vesicles.

To utilize naturally occurring gas vesicles in a gas delivery or removal system, one embodiment of the present invention entails harvesting and collecting cells that have naturally occurring gas vesicles therein. As previously mentioned, known methods for collecting cells containing naturally occurring gas vesicles employ methods that place too much stress on the gas vesicle. These considerations, however, have not been problematic inasmuch as methods or techniques of collecting naturally occurring gas vesicles have been employed simply for small-scale, laboratory studies, not for future uses as contemplated by the present invention.

The organisms from which the gas vesicles of the present invention are obtained can be cultivated either in open waters, such as lakes and ponds, or in sterile bioreactors having well controlled process conditions. Ultimately, the intended end usage of the gas vesicles plays a significant role in the initial environment that the organism should be cultivated in. For example, uncertain contamination that can be expected in open water cultivation often prohibits the use of gas vesicles obtained therefrom for biological and medical applications. It is therefore preferred to obtain naturally occurring gas vesicles from cells cultured in bioreactors. Furthermore, within bioreactors, the process conditions can be controlled and optimized to achieve desirable cell and gas vesicle productivity. This is especially true where certain characteristics of the cell culture are desirable for cell collection.

Figure 2A:
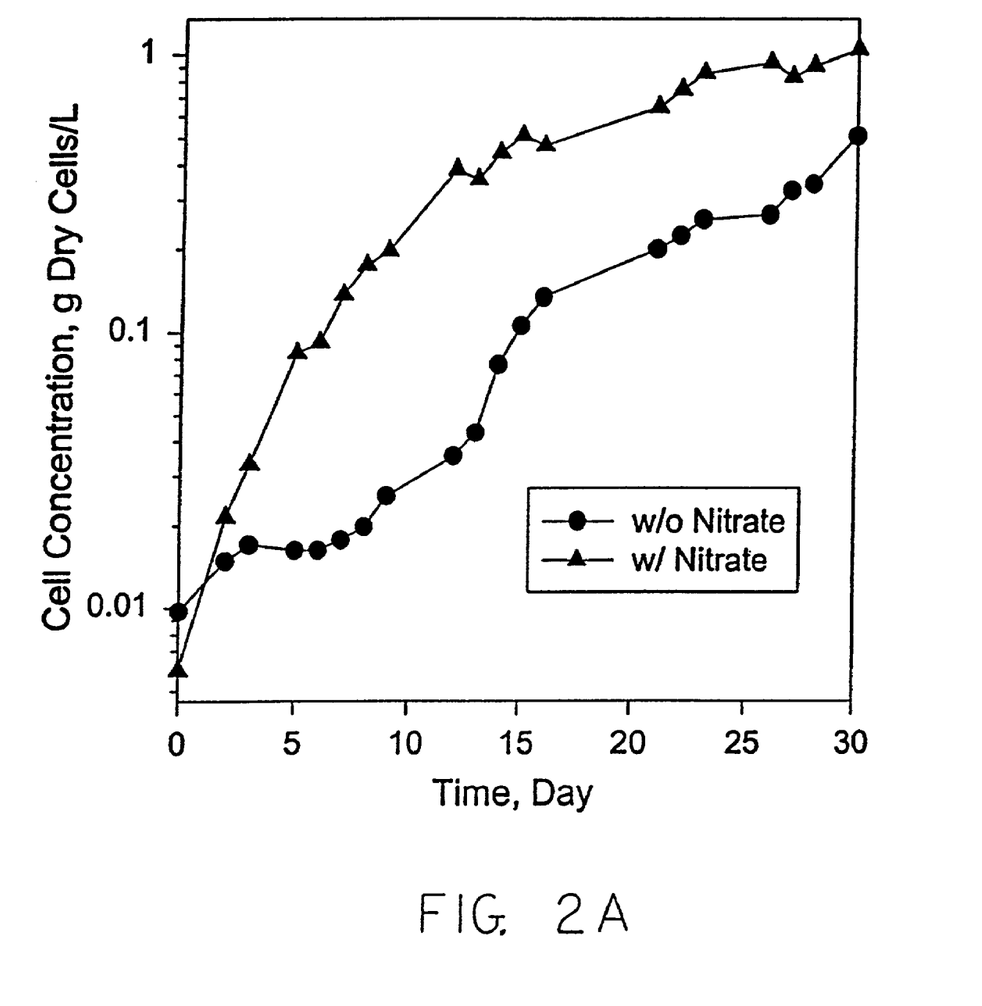
FIGS. 2A and 2B are the effect of nitrate ($NO_3^-$) and light intensity, respectively, on growth of cyanobacteria.

The preferred method of harvesting cells containing gas vesicles includes manipulating environmental and cellular conditions to maximize flotation. With reference to FIG. 2A, it is preferred to culture the preferred cells employed in the present invention in an environment containing nitrate. As can be seen in the data plot of FIG. 2A, the growth of cyanobacteria with nitrate has a higher exponential growth rate and a reduced lag phase. Significantly, it has been found that the cultures are most buoyant and float most rapidly during their exponential growth stage.

It has been found that for the preferred species of bacteria, which are nitrogen-fixing bacteria, a usable nitrogen source in the medium aids in cell growth, thereby enhancing the yield of gas vesicles. If the only nitrogen source in the medium is nitrogen gas ($N_2$), it is believed that the cells must consume large quantities of energy to fix nitrogen, thereby interfering with cell growth. Therefore, a preferred nitrogen source is one that can provide nutrition to the cells while requiring less energy to metabolize than does nitrogen gas ($N_2$).

Although one skilled in the art will realize that many sources of nitrogen are feasible, the preferred sources of nitrogen are ammonium and nitrate ions, preferably added to the medium as a salt. These ions are most preferred because of their low toxicity and low expense. It has been found that bacteria cells grow faster in the presence of ammonium, provided the concentration is kept low. Above about 10 mg $NH_4^+$—N/L, the ammonium ions become toxic to the cells. Therefore, it is most preferred that from about 3 to about 10 mg $NH_4^+$—N/L is provided to the cells by frequently adding small quantities of ammonium salt. Although the cells do not grow as fast with nitrate as with ammonium, higher concentrations of nitrate can be added to the cells without being toxic. Therefore, the addition of one batch of from about 10 to about 100 mg $NO_3^-$—N/L can be used.

It has also been found that cell cultures are more likely to become buoyant and float under dark conditions wherein the cells consume intracellular carbohydrates and become less dense. Therefore, it is preferred to collect cells from the surface of a medium in the dark stage once the cells have had sufficient time to float to the surface. Although the minimum time one must wait depends on the distance the cells must travel to reach the surface, generally about 5 to about 15 hours is ample. Keeping the cells in darkness for more than about 24 hours should be avoided, however, because the cells will begin to die and sink at about this time.

Generally, cell culture growth undergoes an exponential stage, followed by a linear stage and then a stationary or plateau stage. The maximum concentration achieved depends on the growing conditions. One important growing condition is the amount of light the cells are exposed to during growing. It has been found that the best growth occurs when cells are exposed to at least about two watts per square meter; however, at an intensity greater than about 2 klx, the vesicles start to collapse, presumably due to an increase in intracellular, or internal, osmotic pressure. Since the light is most intense at the directly illuminated surface of the medium, the ideal surface light intensity for cultures that are mixed is greater than for cultures that are not mixed. Therefore, an example of one preferred bioreactor is one containing about 5 liters of culture medium stirred at a rate of about 200 rpm under a surface light intensity of from about 1.1 klx to about 2.1 klx.

Accordingly, the cells are preferably cultured in continuous light and placed in the dark when flotation is desired. The light is preferably fluorescent due to its inexpense and availability, but it could also be from other sources of white light or colored light. If colored light is used, it is preferable to use light at about 430 nm and/or about 680 nm because it is believed that these are the peak absorption wavelengths at which light is harvested by the chlorophyll of the cells. Preferably, the light exposure is continuous because it is believed that the cells consume food reserves in the dark and cell growth is slower. Accordingly, a method of collecting cells according to one embodiment of the present invention entails placing the cells, preferably during their exponential growth stage and preferably in a dark environment, so as to cause the cells to float to the surface of the aqueous medium in which they are contained. These cells can then be physically removed from the aqueous medium's surface by suction. One skilled in the art will appreciate, however, that there are other means for physically removing or collecting the cells.

The collection methods described hereinabove can be further improved by inducing flocculation. Flocculation, or aggregation, of the culture to generate large flocs of cells can amplify the effect of density differences and shorten the process time significantly. While the density difference is the driving force for particle flotation or settlement, the speed of the particle movement in the process is proportional to the square of the particle size, deviating significantly only at high cell concentration. Flocculating agents, such as polyethylenimines, polyacrylamides, polyamine derivatives, ferric chloride, and alum, can be added to induce the flocculation process. The skilled artisan will realize, however, that additional flocculating agents, or combinations thereof, could also be used.

According to another embodiment of the present invention, cells can be collected in a non-exponential stage. Indeed, it is desirable to harvest at a later stage for higher cell and, thus, higher gas vesicle concentrations. Since natural buoyancy is diminished in the post-exponential stages of growth, flotation can be achieved by dissolved gas flotation. A liquid, preferably aqueous, is first gas-pressurized to a high pressure to dissolve large amounts of gas in it, preferably about 50 to about 80 atm. One skilled in the art, however, will realize that higher or somewhat lower pressures could also be used. The liquid is then injected into a medium containing the culture under lower pressure, preferably ambient pressure. The sudden pressure drop causes many very fine bubbles to form because the medium becomes over-saturated with gas. The tiny bubbles float to the medium's surface, carrying with them the filaments that they encounter in their path. With this technique the flotation of the cells is achieved primarily due to the buoyancy of the gas bubbles. It is therefore substantially independent of the cell buoyancy and can be applied to the culture harvested at any stage. It should also be noted that the type of gas used is not critical because the gas is merely a carrier. Readily available gases such as air, oxygen, nitrogen, or carbon dioxide, for example, could be employed.

Following collection of the cells, the gas vesicles must be removed from the cells. Removal generally requires lysis of the cell wall, which is achieved by placing the cells in a hypertonic sucrose solution, such as a 0.7 M sucrose solution. Within such an environment, the cells shrink under osmotic pressure and eventually rupture. After the cells have been ruptured, the extracellular gas vesicles can be separated from the waste cell material by filtration or centrifugation methods. It should be appreciated that because there is a large density difference between the gas vesicles and waste cell material and because of the release of intracellular osmotic pressure, techniques such as centrifugation are now useful.

Once extracted and separated from the cell material, the gas vesicles are preferably modified to improve their stability and mechanical strength. Specifically, the present invention provides for crosslinking of the protein surface of the naturally occurring gas vesicles. As a result, the gas vesicles have greater tolerance for fluctuations in temperature or pressure and greater resistance to chemical, microbial or enzymatic agents. It has also been found that crosslinking of the protein surface also serves to sterilize the gas vesicle suspension for long term storage. Most, if not all, crosslinking agents contemplated by the present invention crosslink all proteins found in the medium. Therefore, the enzymes of microorganisms present in the medium also become crosslinked, thereby killing the microorganisms. This crosslinking of the protein surface further serves to render the gas vesicles more suitable for biological and medical applications.

Crosslinking agents that can be employed include any bifunctional crosslinking agent. Examples of such crosslinking agents include bisdiazobenzidine, N,N'-ethylene bismaleimide, hexamethylene diisocyanate, toluene diisocyanate, hexamethylene diisothiocyanate, N,N'-polymethylene bisiodoacetamide, and preferably glutaraldehyde.

Although crosslinking is preferred, gas vesicles can be strengthened or stabilized by other methods, such as interfacial polymerization or encapsulation. Interfacial polymerization is based on diffusion retardation of the polycondensation reaction of two highly reactive difunctional monomers. Two monomers, one inside the gas vesicle and one outside, meet at the interface, the gas vesicle coat, and the fast polymerization reaction forms a thin polymer film at the interface. A crosslinking agent can be used to further increase the strength of the polymer film.

Encapsulation can be achieved by phase separation (coacervation) or by liquid drying methods. Briefly, for coacervation, a polymer is dissolved in an organic solvent and precipitated onto the vesicles by adding another organic solvent that is miscible with the first but does not dissolve the polymer. If the temperature and the amount of organic solvent added are varied, the polymer solution can be separated into two phases containing low and high concentrations of polymer.

For liquid drying, gas vesicles can be suspended in a polymer solution whose solvent is water-immiscible. The suspension is then dispersed in an aqueous solution and dried by warming under a vacuum, for example. The removal of organic solvent leaves a thin coating of the water-insoluble polymer on the surface of the gas vesicles.

Interfacial polymerization and coacervation both add strength to the vesicles. These methods are generally not preferred when gas delivery or removal is the intended application, however, because the surface coatings slow down the mass transfer of gas across the vesicle wall.

Furthermore, it should be appreciated that the crosslinking of the proteinaceous surface improves the stability of the gas vesicle even under the stripping action of SDS. This increased stability is significant because surface-active substances are typically encountered in most pharmaceutical and biological manufacturing processes. It also should be appreciated, however, that this further step of crosslinking, although preferred, is optional.

The amount of crosslinking agent employed is a function of the vesicle concentration in the solution and the type of crosslinking agent. For example, it has been found useful to employ from about 0.001 to about 5% (w/v), preferably from about 0.05 to about 0.15%, and more preferably from about 0.08 to about 0.12% glutaraldehyde in a lysate or other suitable solution. It is preferable to crosslink the gas vesicles before harvesting—while in the lysate—in order to maximize the yield of intact gas vesicles.

It is also preferable to remove excess crosslinking agent from the gas vesicles. In a preferred embodiment of the present invention, where glutaraldehyde is employed, removing excess glutaraldehyde is especially important because it is a toxic substance that would preclude employing the gas vesicles in biological or medical purposes if such residual crosslinking agent were not removed. One method for removing excess crosslinking agent is by successive dialyses of the treated gas vesicle suspension.

Once the naturally occurring gas vesicles of the present invention have been harvested and, optionally, modified, the gas vesicles may then be filled or loaded with a gas to be carried. The gas is loaded by allowing the gas vesicles to equilibrate in the presence of the gas. It should be noted that in a preferred embodiment, gas transfer across the very thin proteinaceous coat of the gas vesicles occurs quickly relative to the diffusion of the gas in the thicker surrounding aqueous or liquid medium. Therefore, the vesicle coat is typically not the rate-limiting step of gas transfer for either the loading or releasing stage.

One preferred use of the gas vesicles of the present invention includes using the gas vesicles as oxygen carriers in biological applications. For example, the gas vesicles, having oxygen loaded therein, can be used to deliver oxygen to cells, whether the cells are isolated or in the form of tissues or organs. This is significant inasmuch as oxygen cannot be directly delivered to animal cell cultures at high rates using traditional methods, such as mechanical mixing, because animal cells are very sensitive to shear forces.

A similar preferred use of the gas vesicles of the present invention includes using the gas vesicles as carriers for the removal of inhibitory or toxic metabolic gases, such as carbon dioxide, nitric oxide, ammonia, volatile alcohols such as methanol and ethanol, and volatile organic acids such as formic acid and acetic acid, in biological applications. For example, the gas vesicles, having a gas with a low partial pressure of carbon dioxide loaded therein, can be used to remove carbon dioxide from cells, whether the cells are isolated or in the form of tissues or organs. As mentioned above, this is significant inasmuch as carbon dioxide cannot be directly removed from certain cell cultures such as animal and insect cells and tissues at high rates using traditional methods, such as mechanical mixing. Even mild shear such as that associated with bubbling, may cause cell death or alteration of the normal activity of the cells. Such a low shear environment, however, leads to poor gas-liquid interfacial transfer and, consequently, potential accumulation of the inhibitory gaseous metabolites.

Furthermore, delivery of one gas and removal of another may naturally occur simultaneously. For example, if gas vesicles are loaded with oxygen, the vesicles can deliver oxygen and remove carbon dioxide at the same time. It is possible, however, for one gas to be delivered without removing another and vice versa. For example, gas vesicles can be loaded with gas that has a partial pressure for oxygen that is equal to that of the medium, but has a lower partial pressure for carbon dioxide than the medium. In such a case, carbon dioxide will partition into the vesicles but oxygen will not diffuse out of the vesicles because of the relative partial pressures of each gas inside and outside the vesicles. A gas will diffuse into or out of the vesicles only to the extent necessary to equalize the partial pressure of that gas inside and outside the vesicles.

Use of gas vesicles may be especially advantageous in biological systems and processes employing high cell densities. High cell density intensifies the generation rates of undesirable metabolic compounds and is often associated with high viscosity of the culture broth because of the large amounts of cells in the suspensions. Membrane bioreactors such as hollow fiber reactors and other cell immobilization techniques are typically used to retain cells and achieve high cell densities. These systems do not allow direct contact between culture broth and the free gas phase to remove metabolic gases effectively.

Furthermore, because oxygen has low solubility in aqueous media, low oxygen and high carbon dioxide concentrations are often encountered in animal cell cultures. These concentrations are sometimes at levels which do not allow complete aerobic functioning of the cells. This directly influences the maximum cell concentration achievable and thereby results in a low product titer and a low process productivity. To overcome these problems, the present invention provides a method whereby oxygen-filled gas vesicles are introduced into the cell or tissue environment to increase the oxygen content and/or to decrease the carbon dioxide content thereof. It is envisioned that for most oxygen-delivery or metabolite-removal uses, the highest achievable concentration of gas vesicles is desirable for maximum oxygen delivery. Although expensive and time-consuming, concentrations up to about 30% (v/v) are possible before being limited by high viscosity. It is envisioned that for most oxygen-delivery or metabolite-removal applications, a gas vesicle concentration between about 0.01 and about 10% (v/v) is effective without undue expense. The cost, however, is also dependent on whether it is feasible or desirable to recover or reuse the gas vesicles at a high concentration. Furthermore, for other uses, such as imaging, lower concentrations may suffice.

To demonstrate the practice of the present invention, the following was performed. It will be appreciated that the present invention, while encompassing all of the following example(s), is not necessarily limited thereto, and that other embodiments and characterizations may fall within the scope of the invention.

EXAMPLE

The filamentous gas vacuolate cyanobacterium strain *Anabaena flos-aquae* CCAP 1403/13f was obtained from the Institute of Freshwater Ecology, Windermere, UK. The medium used was as follows: 39 mg/L $K_2HPO_4$, 5 mg/L $Na_2CO_3$, 37 mg/L $MgSO_4*7H_2O$, 9 mg/L $CaCl_2*2H_2O$, 12 mg/L $Na_2EDTA$, 1 mg/L $FeSO_4$, 0.51 mg/L $MnSO_4*4H_2O$, 0.046 mg/L $(NH_4)_6Mo_7O_{24}*4H_2O$, 0.71 mg/L $H_3BO_3$, 0.5 mg/L $ZnSO_4*7H_2O$, 0.020 mg/L $CuSO_4*5H_2O$, 0.012 mg/L $Co(NO_3)_2*6H_2O$, and 600 mg/L $NaNO_3$. The original strain was maintained by regular subculturing in 40 mL glass vials and using the original medium. The original medium did not contain any $NaNO_3$.

Cultures were grown in glass columns bubbled with air from aquarium pumps and passed through humidifiers before being dispersed by dispersion stones placed at the bottom of the vessel. Columns of three different sizes with diameters of 5, 6.5 and 14 cm, heights of 27, 35 and 42 cm and with operating culture volumes of 0.5. 1.0 and 5.0 liters, respectively, were used. The temperature of the culture was maintained at 19° C. by placing the 0.5 and 1.0 L vessels in a refrigerated water bath set at that temperature and by passing water from the bath through cooling coils provided in the 5.0 L column. Sylvania 20 W cool white fluorescent lamps were placed around the photobioreactors to provide for illumination. The average surface intensity of the light, measured using a Lutron LX-101 lux meter, was between about 0.2 to 2.1 klx.

Figure 2B:
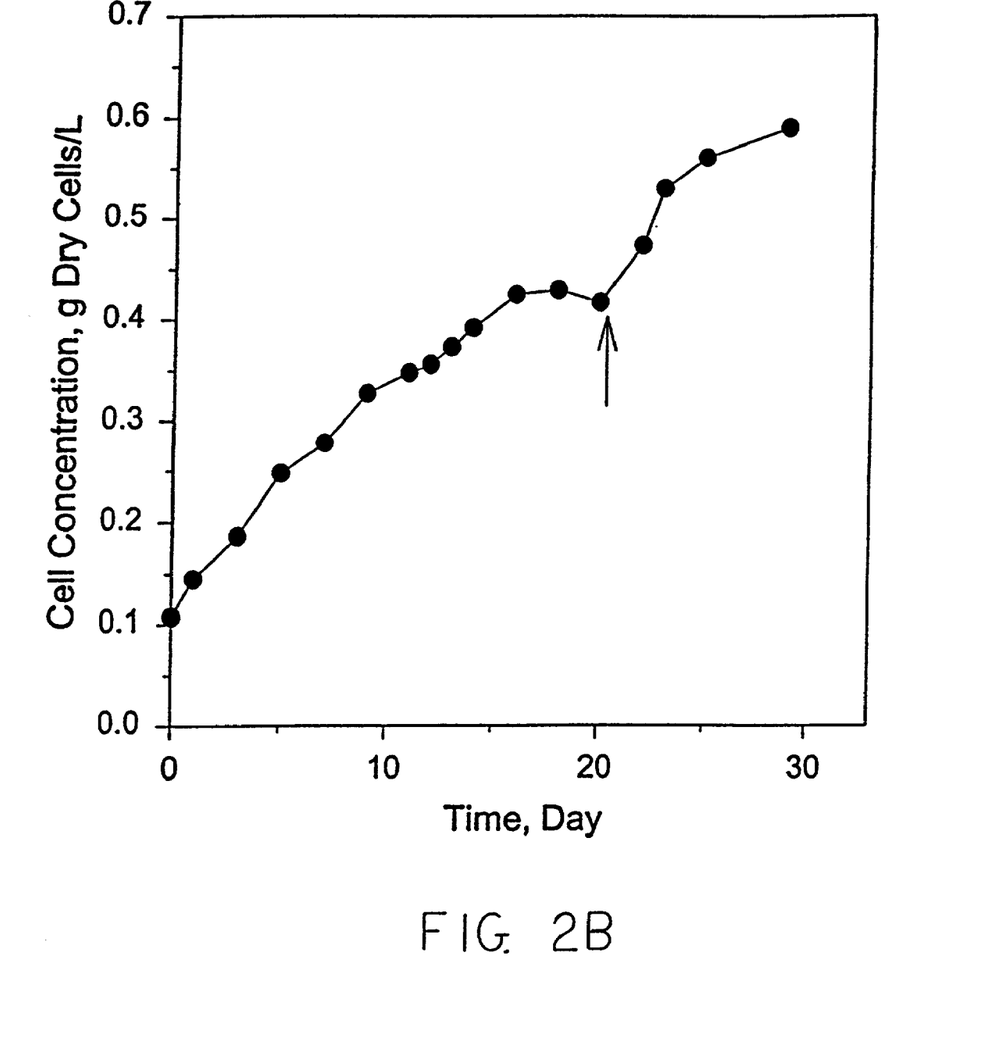

FIG. 2B shows that increasing the light intensity from 1.1 klx to 2.1 klx after 20 days, as indicated by the arrow, caused additional cell growth before plateauing at a higher cellular concentration. As an aside, it should be noted that the cell culture shown in FIG. 2B, although containing nitrate as in FIG. 2A, was grown in a much larger bioreactor, had a higher initial inoculant, and had a higher light intensity (growth in FIG. 2A was under a light intensity of 0.3 klx). This accounts for the higher cell concentration shown in FIG. 2B relative to that shown in FIG. 2A.

The starting pH of the media was maintained at 7.5 and was followed during the fermentation using an Orion pH meter (model 420A). The pH electrode was calibrated in the range of 7 to 10, with appropriate buffer solutions, prior to the measurement of pH. The measurements were made within 10 minutes of taking the samples in order to minimize the effect due to any physiological changes that the cells may undergo.

A calibration curve between the optical density and the cell dry weight was generated. Optical density measurements on culture samples were made using a Perkin-Elmer UV/VIS Spectrophotometer (model Lambda 3B) at a wavelength of 685 nm. Appropriate dilutions were made if the optical densities were beyond the Beer's law range. Dry cell weight was measured by first collapsing the gas vesicles in a 50 mL sample of known optical density, centrifuging the cells, withdrawing the clear supernatant, washing the cells by resuspending and recentrifuging in distilled water, resuspending again in distilled water and drying the cells at 90° C. for 24 hours.

Exponentially growing cells with an optical density of about 1.0 to 1.5 had ideal flotation characteristics and floated rapidly (within 15 hours) to the surface, when the culture was left undisturbed in the dark. Flotation was achieved by placing the culture in graduated cylinders in the dark. The cylinders varied in size from 25 mL to 5.0 L. Flotation was quantified in terms of the rate of rise of filaments to the surface of the undisturbed culture and by the clarity of the subnatant. This phenomenon can be explained by looking at the profiles for cell density, gas vesicle content and the % buoyant filaments.

Figure 3:
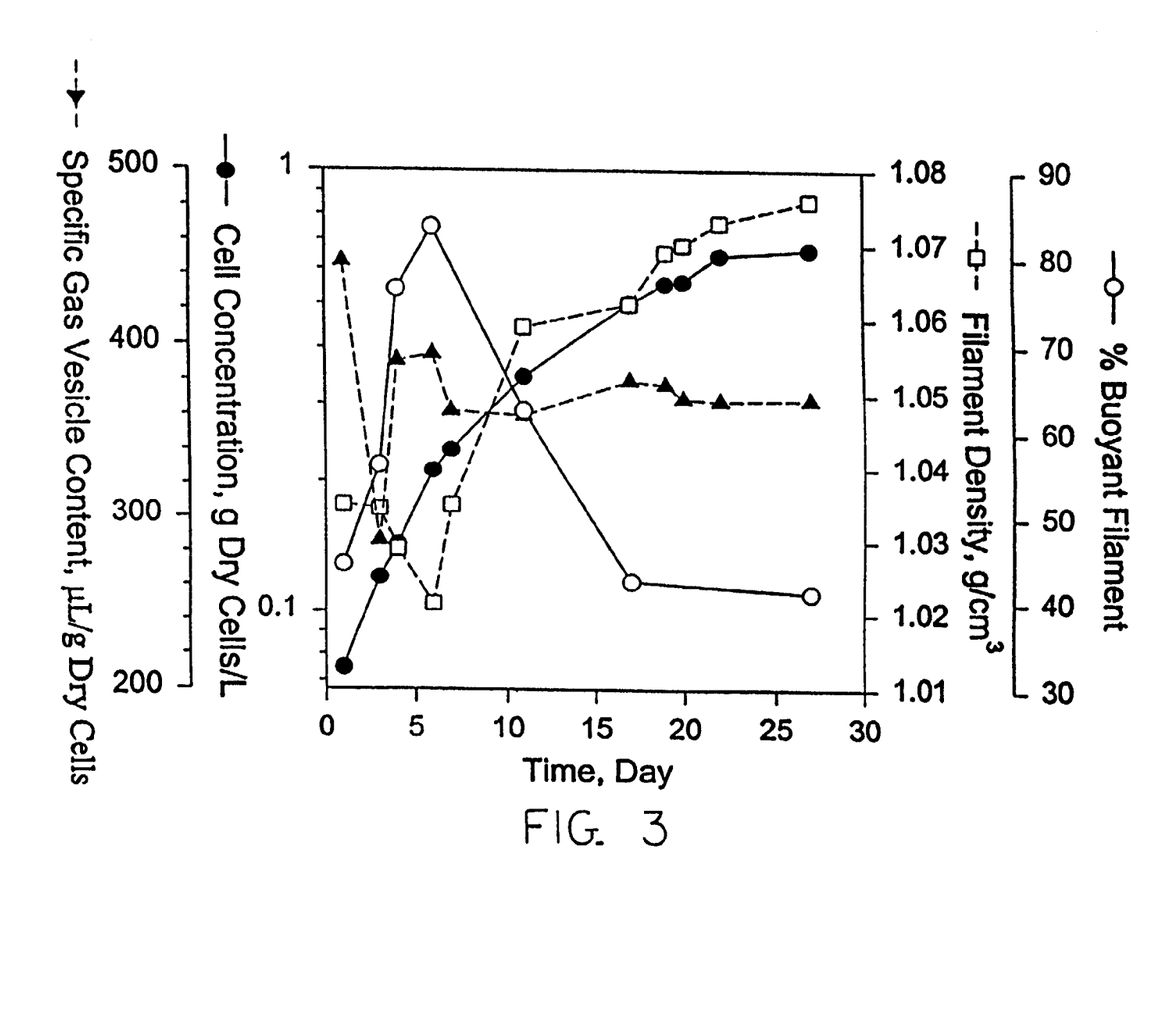
FIG. 3 is profiles of cell concentration, cell density, specific gas vesicle content and percent buoyant filaments from a batch culture of *Anabaena flos aquae*.

With reference to FIG. 3, the increased buoyancy and decreased filament density of cells during their exponential growth stage is represented. Also represented is the specific gas vesicle content, i.e., the gas vesicle concentration per unit cell, which remains relatively constant at various growth stages. The initial fluctuation shown in the graph is due to the experimental uncertainties associated with the measurement of very low cell concentrations.

Figure 4:
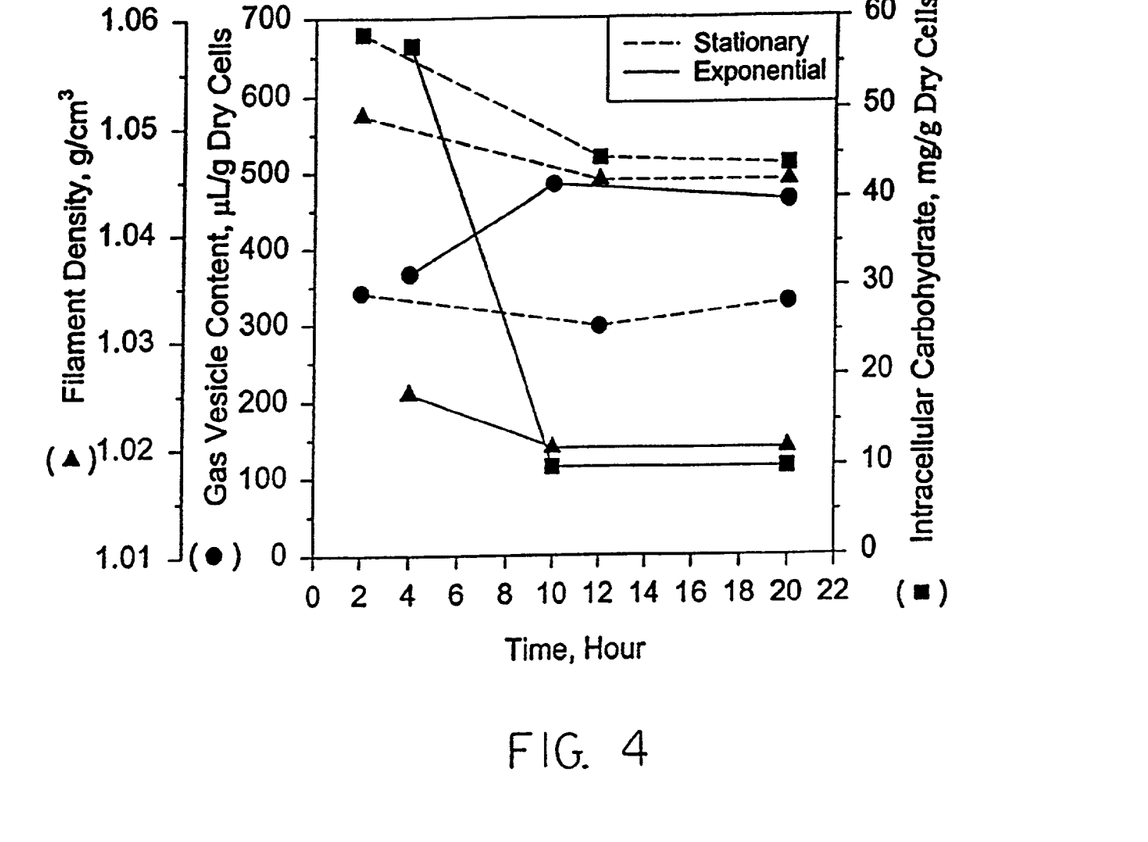
FIG. 4 is a 20-hour batch flotation study for evaluating the effect of culture growth phase on buoyancy.

FIG. 4 demonstrates the advantage of collecting the cultured cells during their exponential growth stage by the flotation method. At various stages of cell growth, flotation was achieved by placing the cells in darkness for about 20 hours. For the cells at the exponential growth stage, it is clear that as the carbohydrate concentration within the cell drops, so does the cellular density.

Cell lysis was done by osmotic shrinkage of the cells when placed in strongly hypertonic sucrose solutions. The cell wall is placed under tension and tends to rupture. Osmotic shrinkage has been tried before but our method was modified to improve the recovery of gas vesicles. Instead of adding an equal volume of 1.4M sucrose solution to the concentrated cells and reducing the final sucrose concentration to 0.7M, which was done previously by others, we modified the method in order to reduce the volume for the centrifugation step. The harvested/concentrated cell suspension was divided into two equal volumes. To one half, crystalline sucrose was added to a concentration of 1.4M. It was dissolved by rapid mixing (gentle stirring) with hand after which the other half was added to give a final sucrose concentration of 0.7M. This way we reduced the operating volume by half, without losing any gas vesicles, and was found to be very beneficial. Secondly we eliminated the use of magnetic stirring as recommended by others as we found that it led to gas vesicle loss due to grinding action. Lysis was complete after the suspension was left at room temperature for 2 hours, during which time the flask containing the lysate was gently swirled every half hour for 1 minute. On completion of lysis (after 2 hours) the lysate was placed in the refrigerator and was kept there at all times prior to gas vesicle isolation.

Figure 5:
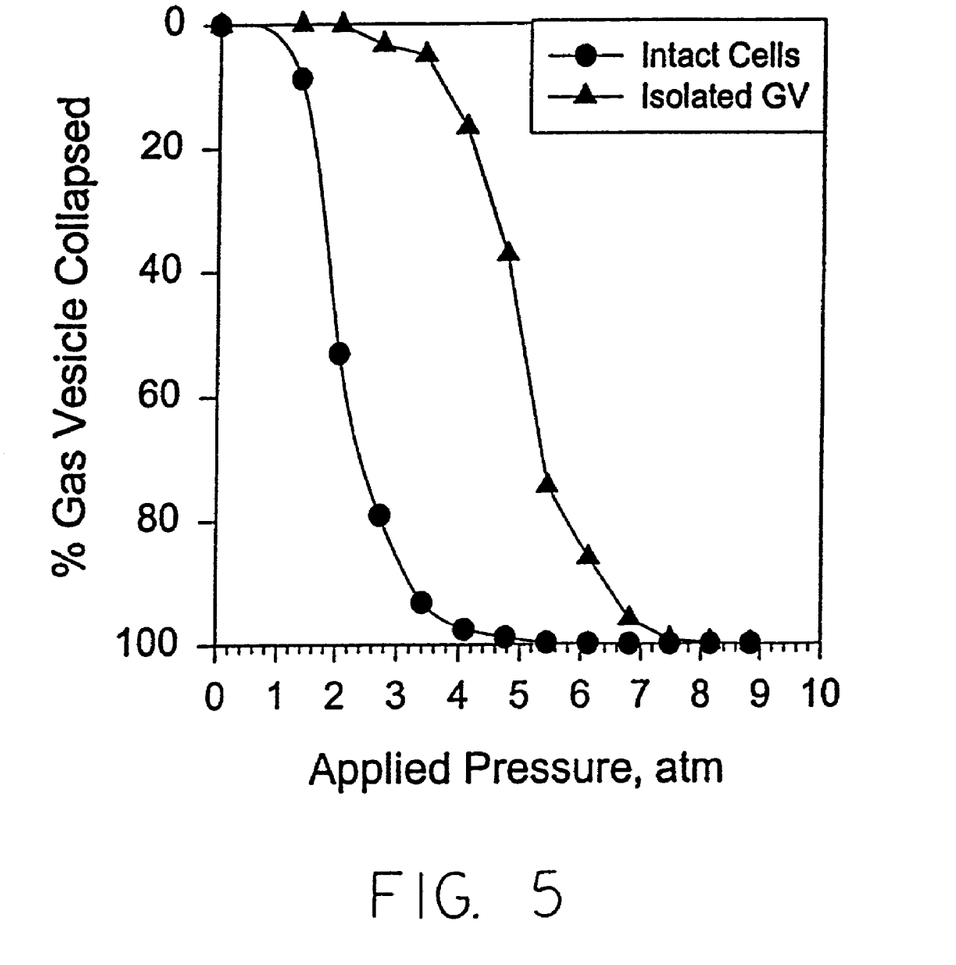
FIG. 5 is pressure collapse curves for gas vesicles of *Anabaena flos aquae*.

FIG. 5 shows that the stability of the gas vesicles, when isolated from the cell, is improved. This is presumed to be due to the fact that intracellular turgor pressure is absent after lysis. Intact gas vesicles have a very low density (ca. 100 kg m$^{-3}$) and despite their small size float up more rapidly than any other cell components. The process can be accelerated by centrifugation, though this may generate sufficient pressure to cause their collapse. Since maximum pressure generated is at the base of the centrifuge cup, the highest possible acceleration is given by a=p/hρ, where p is the minimum critical collapse pressure of the gas vesicles (i.e., the lowest pressure at which there is any gas vesicle collapse), h is the height of lysate in the cup, and ρ is the density of the lysate.

The lysate was centrifuged at 1500 rpm in test tubes filled to a height of 5 cm (ca. 8 mL/tube) for 8 hours. This was based on a minimum critical collapse pressure of 2 atmospheres. The lysate was layered on top with a 5 mm layer of phosphate buffer which helped rinse the vesicles. The gas vesicles were collected from the top using a pasteur pipet with the tip of the pipet held just in contact with the meniscus at the wall of the tube. The gas vesicles were next passed through a 1.4 micron filter to remove any contaminating cells that might have floated up with the gas vesicles and then resuspended in distilled water and recentrifuged.

Suspensions of both isolated gas vesicles and gas vacuolate cells scatter light strongly. Most of the light scattering is due to the gas space rather than the enclosing gas vesicle wall; the amount of light scattered decreases by 98% or more when gas vesicles are collapsed by pressure. The scattered light can be measured directly in a pressure nephelometer to give a relative measure of gas vesicle content.

A Hach Model 2100 A Turbidimeter was used for making pressure nephelometric measurements. The nephelometer was first calibrated using given standards. A thick-walled glass tube filled with 7 mL of either the gas vesicle or the gas vacuolate cell suspension was next inserted into the nephelometer with the pressure-tight coupling attached. A lid was then used to completely cover the tube so that there was no interference due to external light falling on the sample. With the outlet valve closed, the inlet valve was slowly opened and the pressure raised in steps of 10 psi (about 0.7 atm). The light-scattering reading (Nephelometric Turbidity Unit, NTU) falls as gas vesicles are collapsed under pressure. The reading was left to stabilize at each step for a few seconds before proceeding to the next. No further decrease in NTU is an indication that all gas vesicles have collapsed. On releasing the pressure there is no increase in the turbidity, implying the irreversible collapse of gas vesicles.

The volume of gas vesicle gas space in a sample was determined from the contraction caused by application of pressure in a capillary compression tube. The precision bore capillary of 200 micron diameter (31.4 nL/mm) and the attached reservoir (ca. 2.5 mL) are filled with either the gas vesicle suspension or the gas vacuolate cell suspension depending on the experiment. The reservoir end is then closed with a wetted nylon stopper which makes the socket air tight. The tube is then carefully checked for any air bubbles that might be trapped inside, in which case the procedure is repeated. The capillary tube is then placed inside the thick-walled glass pressure tube which is maintained at 18° C. by passing cooling water through the outside water jacket. The reservoir end of the assembly is then sealed by using a threaded plug. Air is sucked into the top centimeter or two of the capillary as the sample cools down. The assembly is next tilted slightly and the pressure tube completely filled with water. At this point water gets pulled into the capillary resulting in a trapped bubble. The other end of the pressure tube is connected to a compressed air cylinder with a pressure gauge. The assembly is then mounted on a movable steel base which is connected to the free end of the sliding arm of a vernier calliper. A microscope fixed on top of the assembly focuses on the meniscus of the air bubble closer to the reservoir end.

The meniscus is allowed to stabilize and the reading on the vernier noted (a). The chamber is next pressurized to 150 psi (ca. 10 atm) upon which the bubble contracts. The meniscus reading (b) is again noted after it stabilizes. Two more readings are taken on the sample: one after releasing the pressure (c) and the other upon repressurizing to 150 psi (d). Gas vesicle volume can be calculated from the value [(a–b)–(c–d)]. All measurements were made in inches from the vernier scale.

The density of cyanobacteria was measured by isopyenic banding on continuous gradients of the silica sol, Percoll, which is a registered trademark of Pharmacia Fine Chemicals. Gradients were formed by centrifuging 10-mL samples, consisting of 2× concentrated cell-free culture medium (5 mL) and Percoll (5 mL), at 32000 g for 1 hour at 5° C. in a fixed angle rotor. This gave a smooth gradient ranging in density from 1000 to 1200 kg m$^{-3}$. The gradient was overlaid with 1 mL of the culture and recentrifuged at 100 g for 20 minutes in a swing-out centrifuge. The filaments formed a visible isopycnic band. The density of this band was determined by using density marker beads which were used to calibrate the gradients. They were used as an external standard, i.e., in a centrifuge tube run simultaneously with the one containing the experimental sample.

Crosslinking of gas vesicles was attempted by treating gas vesicle suspensions with glutaraldehyde. Different concentrations of glutaraldehyde were tested, ranging from 0.001% (w/v) to 5% (w/v). 0.200 mL of a concentrated gas vesicle suspension were added to 7 mL of 0.1 M phosphate buffer. These values were used in order to obtain an initial nephelometric turbidity reading of about 35 units, which was found to be ideal in terms of the range of turbidity available to generate pressure collapse curves. Glutaraldehyde was next added from a 25% (w/v) solution to different vials containing the gas vesicle solution to obtain concentrations ranging from 0.001 to 5% (w/v). One vial was kept as a control with no glutaraldehyde. The reaction was allowed to run for 3 hours. After this treatment, pressure collapse curves were generated for all the samples using the pressure nephelometer.

Figure 6:
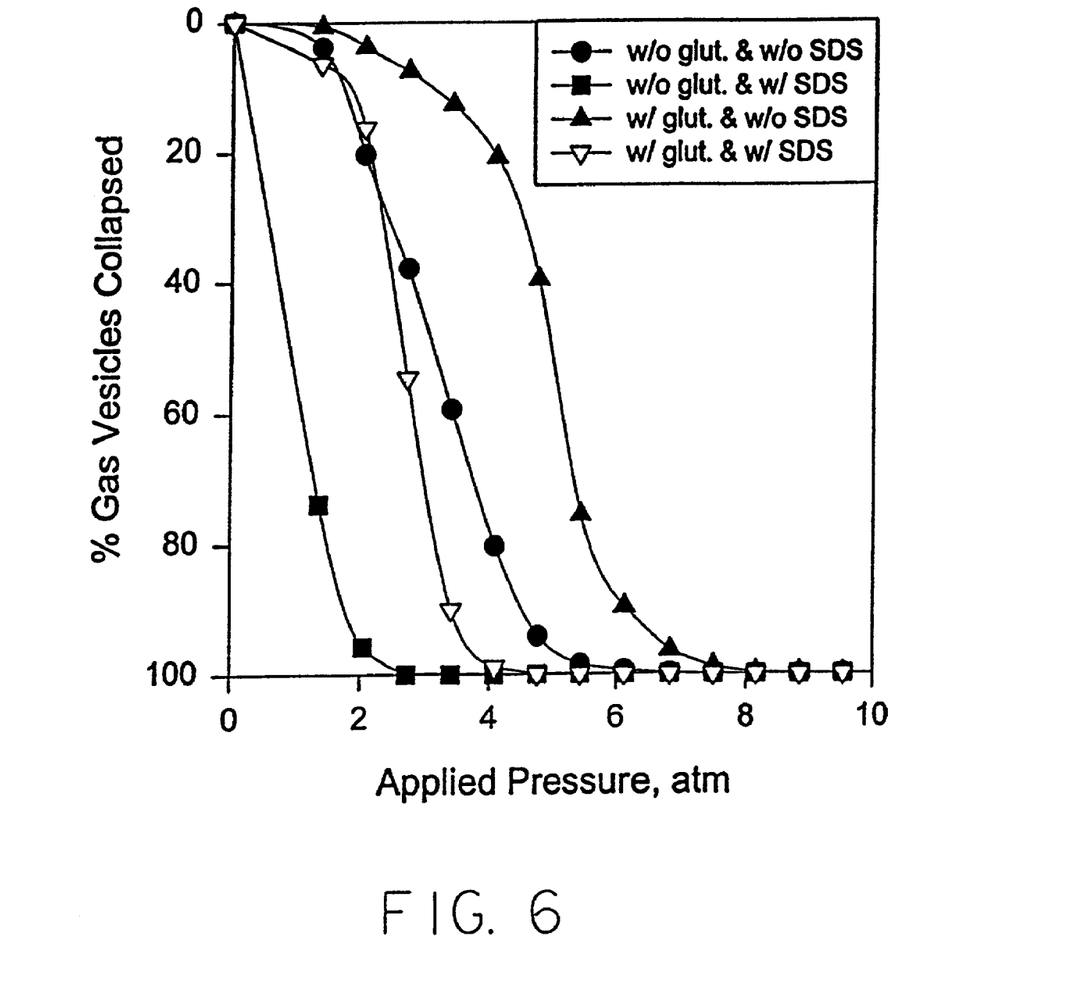
FIG. 6 is the effect of glutaraldehyde treatment of gas vesicles on exposure to 2.5% (w/v) SDS.

With reference to FIG. 6, the improved stability provided by crosslinking of the proteinaceous surface of the gas vesicle is depicted. As can be seen, at about 4 atm of applied pressure, only about 20 to about 30% of the gas vesicles collapsed after being crosslinked by glutaraldehyde in the absence of the surfactant sodium dodecylsulfate (SDS). Detergents like urea (6M) and SDS (2.5% w/v) have been found to significantly weaken gas vesicles due to the stripping of GvpC. Experiments were done to see if glutaraldehyde treatment to crosslink the gas vesicles reduced protein stripping by these detergents. This will provide a measure of the extent of crosslinking achieved.

0.4 mL of concentrated gas vesicle suspension were mixed with 3.5 mL of 0.1 M phosphate buffer at pH 8.0.

Glutaraldehyde was added to make a concentration of 0.1 % (w/v) and the treatment was done for 3 hours. 3.5 mL of 12 M urea was then added to the treated samples. Since SDS was found to precipitate in 0.1 M phosphate buffer, nephelometric turbidity measurements could not be made on samples containing SDS. As a result, 0.4 mL of concentrated gas vesicle suspension were mixed with 3.5 mL of distilled water and the pH adjusted to 8.0. 3.5 mL of 5% (w/v) SDS were mixed with an equal volume of the gas vesicle containing sample. Gas vesicle collapse curves were generated by pressure nephelometry on the samples rinsed with SDS.

Figure 7:
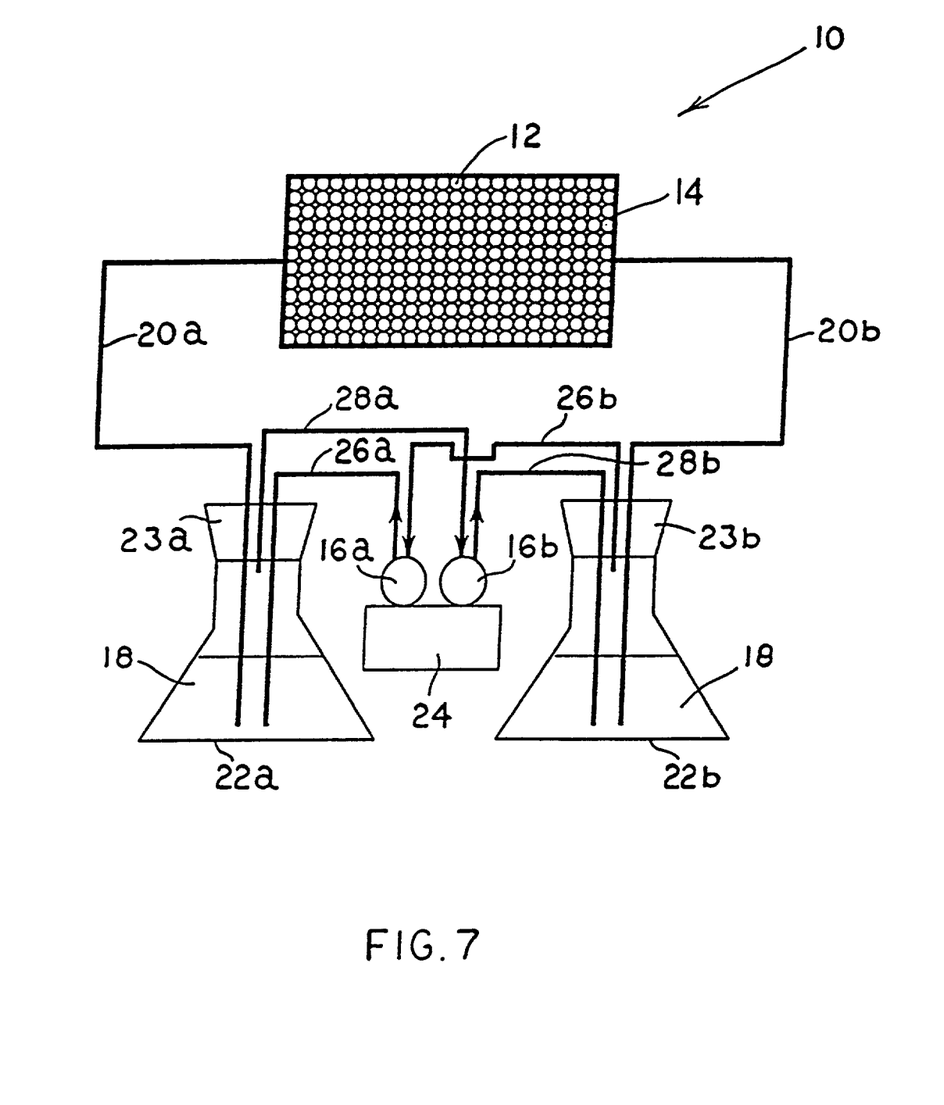
FIG. 7 is an apparatus for evaluation of oxygen supply and carbon dioxide removal capacity of gas vesicles in animal cell culture.

The ability to deliver oxygen and to remove carbon dioxide was demonstrated using a perfusion culture of Vero cells according to the experimental set up represented generally by the numeral 10 in FIG. 7. Vero cells are kidney cells of the African green monkey having an average cell size of about 25 μm. Vero cells are an anchorage-dependent cell line and need a substratum upon which to proliferate. They were therefore grown on glass microcarrier beads 12 with an average diameter of about 180 μm. Beads 12, having attached Vero cells, were packed into a thin glass column 14 having a diameter of about 1 cm and a volume of about 5 mL. Using a set of pumps 16a and 16b, a culture medium 18 was perfused back and forth through tubing 20a and 20b and column 14 at a rate of 0.56 mL per minute from reservoirs 22a and 22b, sealed by stoppers 23a and 23b, respectively. An on/off controller 24, having two independently programmable timers, controls the perfusion. Pump 16a controls the clockwise flow of medium 18 by pumping air clockwise through conduits 26a and 26b. Likewise, pump 16b controls the counterclockwise flow of medium 18 by pumping air counterclockwise through conduits 28a and 28b.

Figure 8:
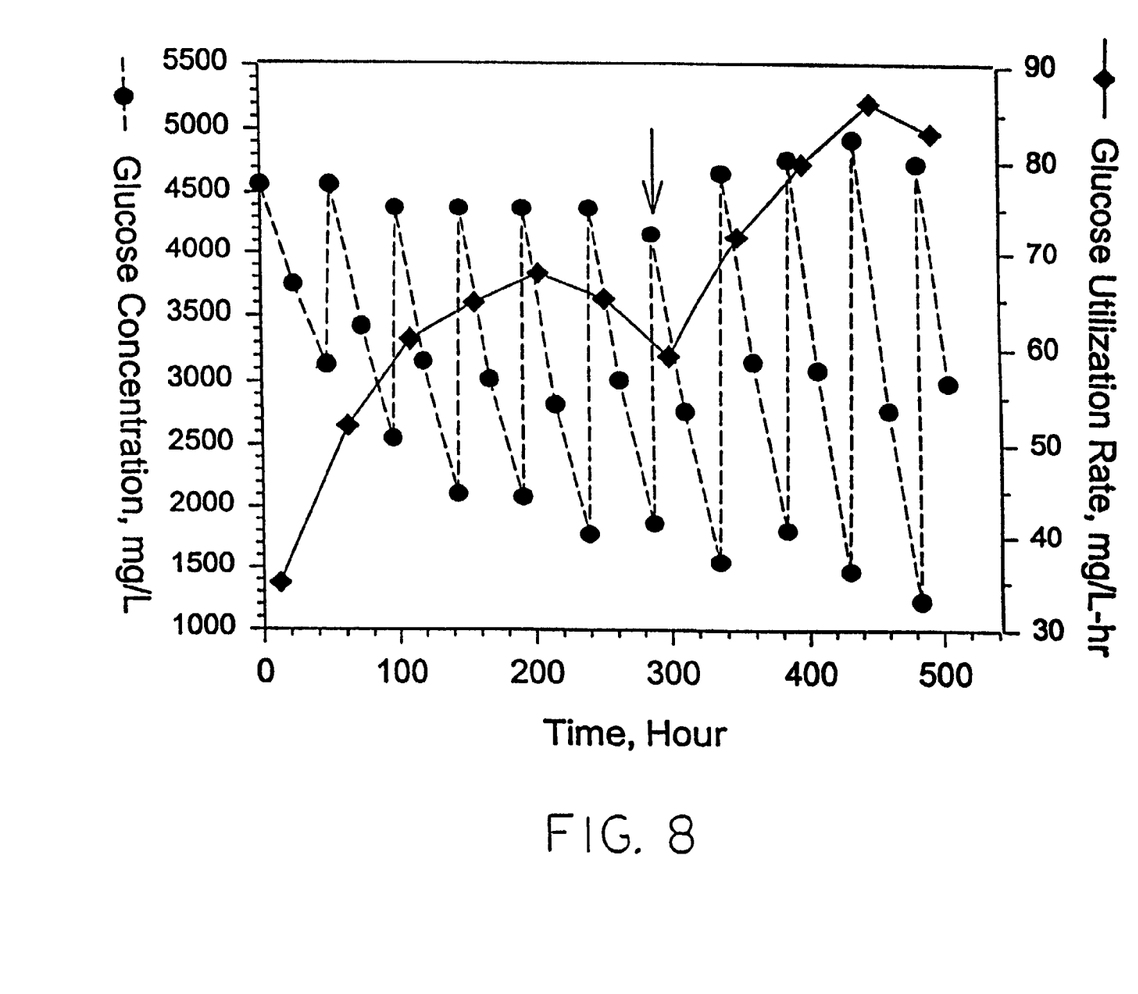
FIG. 8 is profiles of glucose concentration and glucose utilization rates in a perfusion run with DMEM containing 1% serum and later supplemented with 1.8% gas vesicles.

The cell growth profile was followed with time, adding glucose periodically to maintain the concentration of glucose between about 1000 and about 5500 mg/L. The glucose utilization rate, which is proportional to cell concentration, was used as a proxy for cell concentration. The growth eventually plateaued, presumably due to either limited oxygen availability, since all other essential nutrients were available, or inhibition caused by accumulation of carbon dioxide in the medium or both. At this point, the culture medium was supplemented with gas vesicles of the present invention such that the culture medium contained about 1.8% (v/v) crosslinked gas vesicles. As can be viewed in FIG. 8, after the addition of gas vesicles, indicated by the arrow, the cell concentration increased at least 20%. This demonstrates the improved oxygen and carbon dioxide carrying capacity of gas-vesicle-supplemented media. The biological compatibility of the gas vesicles of the present invention should also be appreciated.

Therefore, it is contemplated that gas vesicles can be used to deliver a gas to a site or to remove a gas from a site, whether the site is animate or inanimate matter. As long as gas vesicles can be moved to an environment whereby the gas inside the vesicle can diffuse out or the gas outside the vesicle can diffuse in, delivery or removal of a gas can be achieved. For example, the present invention can be used to deliver oxygen to and/or remove carbon dioxide from cells—whether those cells are of the same type or different, as in the case of tissues or organs—either in vitro or in vivo. It is envisioned that this will typically be done by putting gas vesicles into a liquid medium, allowing the oxygen to diffuse from the vesicles into a liquid medium and/or allowing the carbon dioxide to diffuse from the medium into the vesicles, and allowing the oxygen-enriched, carbon dioxide-depleted medium to flow over the cells and effect gas transfer. However, it is also envisioned that gas can be removed from a site via gaseous (e.g., air) or solid media, or possibly even by direct contact with the site, without an intermediate transferring medium.

It is further contemplated that the gas vesicles of the present invention can be used to treat mammalian cancers or tumors in conjunction with radiation therapy. Species of tumors exist where, due to rapid growth, localized hypoxic (oxygen depleted) zones exist. These hypoxic cells are not amenable to traditional radiation therapy without endangering healthy tissue. Radiation therapy has been shown to be more effective by increasing the local oxygen partial pressure around the tumor area. It is envisioned that the injection of gas vesicles can accomplish this.

Furthermore, gas vesicles may be used as contrast agents for diagnostic ultrasound. Diagnostic ultrasound is a tool to gain insight into the state of internal organs of the body, but its use remains limited in the imaging of certain metastatic lesions. The use of a contrast agent to improve the imaging has been proposed. Gas vesicles may replace polymer-coated microbubbles because polymer coated microbubbles are larger in size. For such a use, the concentration of gas vesicles need only be about 0.1% (v/v), or possibly as low as 0.01%, to be effective.

Thus it should be evident that the device and methods of the present invention are highly effective in obtaining naturally occurring gas vesicles and employing them in biological or medical applications. The invention is particularly suited for oxygen delivery and carbon dioxide removal, but is not necessarily limited thereto. The device and method of the present invention can be used separately with other equipment, methods and the like.

It is, therefore, to be understood that any variations evident fall within the scope of the claimed invention and thus, the selection of specific component elements can be determined without departing from the spirit of the invention herein disclosed and described. Moreover, as noted hereinabove, other means for modifying the gas vesicle can be substituted for the glutaraldehyde. Thus, the scope of the invention shall include all modifications and variations that may fall within the scope of the attached claims.

What is claimed is:

1. A method of modifying naturally occurring gas vesicles comprising:
   a) placing cells having naturally occurring gas vesicles under conditions that induce the cells to rise to a surface of an aqueous medium,
   b) harvesting the cells under darkness from the surface of the medium,
   c) lysing the cells to form a lysate comprising naturally occurring gas vesicles,
   d) crosslinking the naturally occurring gas vesicles in the lysate with a crosslinking agent in an amount of from about 0.001 to about 5% (w/v), and
   e) separating the modified naturally occurring gas vesicles.

2. The method according to claim 1, wherein the cells are in an exponential growth stage.

3. The method according to claim 1, further comprising inducing flocculation in step a.

4. The method according to claim 1, further comprising of inducing flotation with a dissolved gas in step a.

5. The method of according to claim 1, wherein the cells are selected from the group consisting of cyanobacteria, halobacteria, phototrophic bacteria, and aquatic non-phototrophic bacteria.

6. The method according to claim 1, further comprising the step of:
   prior to step a culturing the cells in substantially continuous light and, optionally, in the presence of a nitrogen source, wherein the nitrogen source is more easily metabolized by the cells than is nitrogen gas.

7. The method according to claim 1, wherein the amount of the crosslinking agent is from about 0.05 to about 0.15% (w/v).

8. The method of modifying naturally occurring gas vesicles according to claim 1, wherein the quantity of the crosslinking agent is from about 0.08 to about 0.12% (w/v).

9. The method according to claim 1, wherein the crosslinking agent is selected from bisdiazobenzidine, N,N'-ethylene bismaleimide, hexamethylene diisocyanate, toluene diisocyanate, hexamethylene diisothiocyanate, N,N'-polymethylene biisodoacetamide, or glutaraldehyde.

10. The method according to claim 9, wherein the crosslinking agent is glutaraldehyde.

* * * * *